United States Patent [19]
Asano et al.

[11] 3,971,735
[45] July 27, 1976

[54] METHANOL PRODUCTION CATALYST AND PROCESS FOR PREPARING THE SAME

[75] Inventors: Setunobu Asano; Tadashi Nakamura; Yasuo Yamamoto, all of Niigata, Japan

[73] Assignee: Mitsubishi Gas Chemical Company, Inc., Tokyo, Japan

[22] Filed: Oct. 21, 1974

[21] Appl. No.: 516,872

[30] Foreign Application Priority Data
Oct. 24, 1973  Japan.............................. 48-119764

[52] U.S. Cl................................ 252/432; 252/463; 260/449 M
[51] Int. Cl.²..................... B01J 21/02; B01J 21/04; B01J 23/06; B01J 23/72
[58] Field of Search........................... 252/432, 463; 260/449 M; 106/73.4

[56] References Cited
UNITED STATES PATENTS

| | | | |
|---|---|---|---|
| 3,703,386 | 11/1972 | Dietz............................. | 106/73.4 X |
| 3,790,505 | 2/1974 | Casey et al. ........................ | 252/463 |

*Primary Examiner*—W. J. Shine
*Attorney, Agent, or Firm*—Haseltine, Lake & Waters

[57] ABSTRACT

A copper, zinc, aluminum and boron catalyst is used as a low temperature methanol synthesis catalyst. The proportions of the catalyst components, in terms of metal atoms, are 30–70% of copper, 15–50% of zinc, 1–16% of aluminum and 0.3–5.3% of boron. This catalyst is prepared by adding an alumina sol to the mixture of copper, zinc and boron compounds and firing the total mixture.

7 Claims, No Drawings

METHANOL PRODUCTION CATALYST AND PROCESS FOR PREPARING THE SAME

This invention relates to a catalyst which is high in catalytic activity, excellent in heat resistance and durability, and preferably for methanol synthesis under relatively low pressures, and to a process for preparing the same.

As catalysts for production of methanol from carbon monoxide and hydrogen, there have frequently been used hitherto catalysts composed of copper-zinc or copper-zinc-chromium, in general. These catalysts, however, are relatively low in heat resistance and durability, though high in activity in general, and hence cannot be successfully usable over a long period of time. Recently, techniques for production of methanol under medium and low pressures of about 50 to 150 kg/cm² have come to be highlighted for the saving of compression power costs, and such catalysts higher in activity are required. For such purpose, there have been proposed copper-zinc-aluminum ternary catalysts (Japanese Patent Publication Nos. 16,682/1970 and 23,263/1973). However, these catalysts also are not sufficient in catalytic activity or heat resistance and durability, and the development of more excellent catalysts has been desired. The present invention provides a methanol production catalyst having excellent properties which has overcome the above-mentioned disadvantages.

The catalyst of the present invention is comprised of oxides of copper, zinc, aluminum and boron, and can be prepared by adding an alumina sol to a mixture of copper, zinc and boron compounds, and then subjecting the total mixture to firing.

The proportions, in terms of metal atoms, of the catalyst components constituting the present catalyst are 30 to 70% of copper, 15 to 50% of zinc, 1 to 16%, preferably 3 to 12%, of aluminum, and 0.3 to 5.3%, preferably 0.5 to 3.5%, of boron.

As the copper and zinc sources in the catalyst of the present invention, water-soluble salts such as nitrates and acetates are used, like in the conventional copper-zinc catalysts. As the boron source, there is used a water-soluble boron compound such as borax, ammonium borate or boric acid. As the aluminum source, sodium aluminate or the like water-soluble salt is extensively used. In the present catalyst, boron is used as a catalyst component, whereby the catalyst is markedly enhanced in activity and improved in heat resistance and durability. Further, the aluminum component imparts mechanical strengths to the catalyst and acts synergistically with the boron component to greatly increase the catalyst in heat resistance and durability.

For preparation of the present catalyst, it is preferable that water-soluble salts of copper, zinc and boron are first mixed together and then an alumina sol is added to the resulting mixture, or a solution of the said salts is charged with alkali carbonate or the like to co-precipitate the metal components and then an alumina sol is added thereto. It should be noted that the aluminum component should necessarily be added to other three components having been combined. In case only the boron component is added later, the resulting catalyst is degraded in activity. Further, in case the aluminum component is co-precipitated together with the other three components, no excellent activity can be attained. The alumina sol to be added is desirably in the form of highly dispersible fine particles having an average diameter of less than 1 $\mu$, preferably less than 200 m$\mu$. The use of an alumina sol coarse in particle diameter results in inferior effects. As the alumina sol, there is used one which can be stabilized with an organic acid or the like and which can maintain the stable state over a long period of time. It is needless to say that the alumina used should not have been migrated with such substances as to have poisoning action on copper-containing catalysts. The copper-zinc-boron co-precipitate, to which the alumina sol has been added, is fired at a temperature of 300° to 450°C. and reduced, if necessary after kneading, molding and drying, whereby a methanol synthesis catalyst high in activity and excellent in heat resistance and durability can be obtained.

The feed gas to be contacted with the catalyst of the present invention to produce methanol is not particularly limited in composition, and may be any of those which have heretofore been used.

In the production of methanol by use of the catalyst of the present invention, the reaction pressure is in the range from 20 to 300 kg/cm², preferably from 30 to 150 kg/cm², the reaction temperature is in the range from 150° to 300°C., preferably from 200° to 280°C., and the space velocity is in the range from 2,000 hr⁻¹ to 5 × 10⁴ hr⁻¹.

While the catalyst of the present invention is excellent as a methanol production catalyst, it can display prominent effects also as a catalyst for carbon monoxide conversion reaction, hydrogenation reaction or methanol decomposition reaction, when the conditions are properly selected.

REFERENCE EXAMPLE 1

Preparation of Catalyst A

A mixture comprising 3,624 g. (15 moles) of industrial grade copper nitrate, 3,347 g. (11.25 moles) of industrial grade zinc nitrate and 695.6 g. (11.25 moles) of industrial grade boric acid was dissolved in 37.6 liters of ion-exchanged water to form a solution (i). On the other hand, 3,339 g. (31.5 moles) of industrial grade soda ash was dissolved in 126 liters of ion-exchanged water to form a solution (ii). The solutions (i) and (ii) were individually heated to 80°C., and then mixed with each other. The resulting mixture was stirred at said temperature for 30 minutes, and then stirred with cooling for 2 hours to deposit a precipitate, which was subsequently recovered by filtration and washed. A part of the precipitate was dried at 80°C. for 15 hours, fired in an air stream at a temperature of 375° ± 5°C. for about 2 hours, crushed, incorporated with 3 g. of graphite as a lubricant, and then pelleted to prepare a catalyst A. The catalyst A was ground to 20 to 40 mesh and then reduced with a methanol-producing feed gas at atmospheric pressure. The reduction temperature was gradually elevated in order to avoid rapid increase in heat due to the reduction reaction, and finally the reduction was conducted at 240°C. for 2 hours.

EXAMPLE 1

Preparation of Catalyst B

To 100 g. of the dried precipitate prior to firing in Reference Example 1 were added, with care so as not to form agglomerates, 40 g. of an alumina sol containing 10% of Al₂O₃ (average particle size of Al₂O₃ = 100 m$\mu$ × 10 m$\mu$) and 60 g. of ion-exchanged water, and the resulting mixture was sufficiently kneaded. After kneading for about 1 hour, the mixture was dried at 80°C. to prepare a catalyst B. The composition of the catalyst B was Cu:Zn:B:Al = 56.5:38.1:1.5:3.9 (by atomic ratio). The catalyst B was fired, pelleted and reduced in the same manner as in the case of the catalyst A.

REFERENCE EXAMPLE 2

Preparation of Catalyst C

A solution of 5.7 g. (0.069 mole) of sodium aluminate in 100 ml. of water was incorporated with 18 ml. (0.2415 mole) of nitric acid having a specific gravity of 1.38. Subsequently, the solution was mixed with a solution in 1,300 ml. of water of 100 g. (0.414 mole) of copper nitrate (GR) and 61.6 g. (0.207 mole) of zinc nitrate (GR) to form a solution (i). On the other hand, 109.4 g. (1.032 moles) of $Na_2CO_2$ (EP) was dissolved in 2,100 ml. of water to form a solution (ii).

The solutions (i) and (ii) were individually heated to 80°C. and then mixed with each other under thorough stirring. After stirring for about 2 hours, the resulting mixture was filtered, washed and then dried at 80°C. for 15 hours.

To 29 g. of the dried mixture were added 0.597 g. of boric acid and about 35 g. of ion-exchanged water, and the resulting mixture was dried at 80°C. for 15 hours, and then fired, pelleted and reduced in the same manner as in the case of the catalyst A to prepare a catalyst C. (Cu:Zn:B:Al = 58.8:29.4:1.97:9.8)

REFERENCE EXAMPLE 3

Preparation of Catalyst D

The dried precipitate in Reference Example 1 was fired at 375° ± 5°C. to form a powder. To 100 g. of the powder were added, with care so as not to form agglomerates, 53 g. of the same alumina sol as used in the catalyst B and about 65 g. of ion-exchanged water, and the resulting mixture was sufficiently kneaded and then dried at 80°C. for 15 hours. Thereafter, the mixture was pelleted and reduced in the same manner as in the case of the catalyst A to prepare a catalyst D.

REFERENCE EXAMPLE 4

Preparation of Catalyst E

A solution of 5.7 g. (0.069 mole) of sodium aluminate in 100 ml. of water was incorporated with 18 ml. (0.2415 mole) of concentrated nitric acid (specific gravity 1.38). Subsequently, the solution was mixed with a solution in 2,500 ml. of water of 100 g. (0.414 mole) of copper nitrate (GR) and 61.6 g. (0.207 mole) of zinc nitrate (GR) to form a solution (i). On the other hand, 109.4 g. (1.032 moles) of sodium carbonate (EP) was dissolved in 4,200 ml. of water to form a solution (ii).

The solutions (i) and (ii) were individually heated to 75° to 80°C. and then mixed with each other under thorough stirring. After stirring for about 2 hours, the resulting mixture was filtered, washed and dried. The dried mixture was treated in the same manner as in the case of the catalyst A to prepare a catalyst E.

Results of comparative test using catalysts prepared in Example 1 and Reference Examples 1 to 4 are given below:

The catalysts A to E prepared in the manners as described above were tested by methanol synthesis under the following conditions:

A feed gas having an inlet gas composition of $H_2$ 67%, CO 23%, $CO_2$ 7%, $CH_4$ 1.5% and $N_2$ 1.5% was reacted under a reaction pressure of 140 kg/cm², at a reaction temperature of 240°C. and at an inlet gas space velocity of 10,000 hr$^{-1}$. The activity of each catalyst, in terms of methanol concentration in the exit gas, was as shown in Table 1.

In the table, the methanol concentrations in columns "360°C. 2 hrs." and "360°C. 20 hrs." are, respectively, a value obtained by synthesizing, after measurement of initial activity, methanol at 360°C. for 2 hours and then measuring the methanol concentration in the exit gas at 240°C., and a value obtained by synthesizing, after said 2 hours' methanol synthesis, methanol at 360°C. for additional 18 hours (total 20 hours) and then measuring the methanol concentration in the exit gas at 240°C.

Table 1

| | | Methanol concentration in exit gas (mol%) | | |
|---|---|---|---|---|
| | Catalyst | Initial | 360°C. 2 hrs. | 360°C. 20 hrs. |
| Reference Example 1 | A | 37.7 | 32.0 | 26.0 |
| Example 1 | B | 37.0 | 35.0 | 34.0 |
| Reference Example 2 | C | 25.1 | 22.0 | 17.0 |
| Reference Example 3 | D | 12.0 | 8.3 | 5.9 |
| Reference Example 4 | E | 32.0 | 29.0 | 22.0 |

Further, the catalysts A and B in the form of pellets (longitudinal compressive strength 170 kg/cm²) were individually reduced and stabilized with air. The results of measurement in strength of the catalysts were as shown in Table 2.

Table 2

| | Catalyst | Longitudinal compressive strength (kg/cm²) | Amount of powdered catalyst (in metal cage under rotation) (wt%) |
|---|---|---|---|
| Reference Example 1 | A | 130 | 35.5 |
| Example 1 | B | 155 | 6.8 |

Further, the catalyst B was tested in the same manner as above, except that the pressure was varied to 70 kg/cm², the space velocity to 20,000 hr$^{-1}$ and the temperature to 240°C., to obtain the results as shown in Table 3.

Table 3

| | Catalyst | Methanol concentration in exit gas (mol%) | | |
|---|---|---|---|---|
| | | Initial | 360°C. 2 hrs. | 360°C. 20 hrs. |
| Example 1 | B | 10.0 | 8.5 | 7.8 |

REFERENCE EXAMPLE 5 AND EXAMPLE 2

A mixture comprising 200 g. (0.8278 mole) of industrial grade copper nitrate, 246.2 g. (0.8278 mole) of industrial grade zinc nitrate and 30.6 g. (0.495 mole) of industrial grade boric acid was dissolved in 3,300 ml. of ion-exchanged water to form a solution (i). On the other hand, 210.6 g. (1.9867 moles) of industrial grade soda ash was dissolved in 3970 ml. of ion-exchanged water to form a solution (ii). The solutions (i) and (ii) were individually heated to 80°C. and then mixed with each other under thorough stirring. The resulting mixture was stirred for 2 hours, filtered, washed and then dried at 80°C. for 15 hours. The dried mixture was fired, pelleted and reduced in the same manner as in the case of the catalyst A to prepare a catalyst F. Alternatively, to 100 g. of the dried mixture were added 40 g. of the same alumina sol as in Example 1 and 65 ml. of ion-exchanged water, and the resulting mixture was sufficiently kneaded, dried at 80°C. The dried mixture was fired, pelleted and reduced in the same manner as in the case of the catalyst A to prepare a catalyst G. the catalysts F and G were individually tested in activity to obtain the results as shown in Table 4.

Table 4

| | Catalyst | Methanol concentration in exit gas (mol%) | | |
|---|---|---|---|---|
| | | Initial | 360°C. 2 hrs. | 360°C. 20 hrs. |
| Reference Example 5 | F | 28.2 | 22.0 | 13.7 |
| Example 2 | G | 33.0 | 31.0 | 27.0 |

EXAMPLES 3–4

To 100 g. of the dried precipitate of Reference Example 1 were added 20 g. of the same alumina sol as in Example 1 and 80 g. of ion-exchanged water. The resulting mixture was sufficiently kneaded, dried and then treated in the same manner as in Example 1 to prepare a catalyst H. The above-mentioned procedure was repeated, except that the amount of alumina sol was varied to 60 g., to prepare a catalyst I. The catalysts H and I were individually tested in activity in the same manner as in the case of the catalyst A. The results obtained were as shown in Table 5.

Table 5

| | Catalyst | Methanol concentration in exit gas (mol%) | | |
|---|---|---|---|---|
| | | Initial | 360°C. 2 hrs. | 360°C. 20 hrs. |
| Example 3 | H | 37.3 | 34.0 | 31.0 |
| Example 4 | I | 33.0 | 30.0 | 28.5 |

EXAMPLES 5–6 AND REFERENCE EXAMPLE 6

A mixture comprising 200 g. (0.8278 mole) of industrial grade copper nitrate, 184.7 g. (0.6209 mole) of industrial grade zinc nitrate and 38.4 g. (0.6209 mole) of boric acid was dissolved in 3,000 ml. of ion-exchanged water to form a solution (i). On the other hand, 184 g. (1.736 moles) of soda ash was dissolved in 3,480 ml. of ion-exchanged water to form a solution (ii). Further, 8.7 g. (1.061 moles) of sodium aluminate was dissolved in about 1,000 ml. of ion-exchanged water to form a solution (iii). The solution (iii) was charged with dilute nitric acid (1:1) and adjusted to a pH of about 4, and the resulting alumina trihydrate suspension was added to the solution (i) to form a solution (iv). The solutions (ii) and (iv) were individually heated to 80°C. and then mixed with each other under thorough stirring. The resulting mixture was stirred for about 1.5 hours, filtered, washed and dried.

The dried mixture was treated in the same manner as in the case of the catalyst A to prepare a catalyst J. Alternatively, the solution (iii) was charged with 3.5 times the moles of the sodium aluminate of nitric acid and adjusted to a pH of less than 1.5, and was then added to the solution (i). The resulting mixture was treated in the same manner as above to prepare a catalyst K.

A mixture comprising 100 g. (0.4139 mole) of copper nitrate (EP), 92.3 g. (0.3104 mole) of industrial grade zinc nitrate and 19.2 g. (0.3104 mole) of boric acid was dissolved in 2,000 ml. of ion-exchanged water to form a solution (i). On the other hand, 92.1 g. (0.8692 mole) of soda ash was dissolved in 1,740 ml. of ion-exchanged water to form a solution (ii). The solutions (i) and (ii) were individually heated to 80°C. and then mixed with each other under thorough stirring. The resulting mixture was stirred for 1.5 hours, filtered and washed to obtain a cake. This cake was kneaded with 32 g. of the same alumina sol as in Example 1, and the resulting mixture was dried. The dried mixture was treated in the same manner as in Example 1 to prepare a catalyst L.

The catalyst J, K and L were individually tested in activity in the same manner as in the case of the catalyst A. The results obtained were as shown in Table 6.

Table 6

| | Catalyst | Methanol concentration in exit gas (mol%) | | |
|---|---|---|---|---|
| | | Initial | 360°C. 2 hrs. | 360°C. 20 hrs. |
| Example 5 | J | 34.0 | 32.0 | 29.5 |
| Reference Example 6 | K | 19.6 | 20.7 | 12.0 |
| Example 6 | L | 35.0 | 34.0 | 31.0 |

What we claim is:

1. A catalyst suited for the production of methanol which comprises the oxides of copper, zinc, aluminum and boron, wherein the proportion of catalyst components is 30–70% Cu, 15–50% Zn, 1–16% Al and 0.3–5.3% B, all the percentages being expressed by the metal atom ratio.

2. A catalyst as claimed in claim 1, wherein the proportion of catalyst components is 30–70% Cu, 15–50% Zn, 3–12% Al and 0.5–3.5% B, all the percentages being expressed by the metal atom ratio.

3. A process for the preparation of a catalyst suited for the production of methanol, which comprises adding an alumina sol to the mixture of a water-soluble copper salt, a water-soluble zinc salt and a water-soluble boron compound selected from borax, ammonium borate or boric acid, and then firing the total mixture.

4. A process as claimed in claim 3, wherein the mixture of copper, zinc and boron compounds is a coprecipitate obtained by treating an aqueous solution of water-soluble copper, zinc and boron compounds with an alkali carbonate.

5. A process as claimed in claim 3, wherein said firing is carried out at a temperature of 300°–450°C.

6. A process as claimed in claim 3, wherein said alumina sol is in the form of a dispersion having a particle size of less than 1μ.

7. A process as claimed in claim 3, wherein said alumina sol is in the form of a dispersion having a particle size of less than 200 mμ.

* * * * *